United States Patent [19]

Benedikt et al.

[11] Patent Number: 4,803,080

[45] Date of Patent: Feb. 7, 1989

[54] SUSTAINED-RELEASE THEOPHYLLINE FORMULATION

[75] Inventors: Gerald Benedikt; Volker Steinijans, both of Constance, Fed. Rep. of Germany

[73] Assignee: BYK Gulden Lomberg Chemische Fabrik, Fed. Rep. of Germany

[21] Appl. No.: 811,742

[22] Filed: Dec. 20, 1985

[30] Foreign Application Priority Data

Dec. 21, 1984 [CH] Switzerland .......................... 6111/84
Jun. 24, 1985 [CH] Switzerland .......................... 2683/85

[51] Int. Cl.$^4$ .............................................. A61K 9/14
[52] U.S. Cl. ..................... 424/488; 424/475; 424/480; 424/486; 514/263
[58] Field of Search ............... 424/458, 459, 461, 462, 424/490, 494, 495, 497, 475, 480, 486, 488; 514/263; 427/3

[56] References Cited

U.S. PATENT DOCUMENTS

| | | | |
|---|---|---|---|
| 4,587,118 | 5/1986 | Hsiao | 514/263 X |
| 4,663,150 | 5/1987 | Panoz et al. | 424/497 X |
| 4,692,337 | 9/1987 | Ukigaya et al. | 424/469 |
| 4,704,284 | 11/1987 | Beatty et al. | 424/469 |

Primary Examiner—Michael Lusignan
Attorney, Agent, or Firm—Berman, Aisenberg & Platt

[57] ABSTRACT

A sustained-release theophylline formulation, which comprises matrix pellets in which theophylline particles are embedded in a matrix of water-insoluble plastic and which are enclosed by a membrane of water-insoluble plastic containing embedded particles of lactose, produces and maintains plasma theophylline levels within the therapeutic range.

28 Claims, No Drawings

SUSTAINED-RELEASE THEOPHYLLINE FORMULATION

TECHNOLOGICAL FIELD

The invention relates to a sustained-release theophylline formulation.

BACKGROUND

Theophylline (1,3-dimethylxanthine) is a wellproven medicament for therapy of obstructive diseases of the respiratory tract. Because its pharmacokinetics differ greatly between individuals and it has a very narrow therapeutic range with plasma levels of 8-20 mg/1, it presents exceptional pharmaceutical difficulties in providing a suitable formulation for chronic oral therapy which guarantees, under steady-state conditions, uniform blood levels which are within the therapeutic range and are also maintained during the night. In view of patient compliance, which is particularly important with this drug, an oral presentation form which enables the entire daily dose to be taken at once would be particularly desirable.

German Auslegeschrift No. 2,336,218 describes a depot medicament form with linear release of active compound, which can be used for theophylline and in which spheroid medicament particles are coated with a dialysis membrane, the film-forming agent of which consists of an insoluble cellulose ether and a soluble organic compound containing carboxyl groups. With this depot medicament form, it is possible to achieve linear release of theophylline for 6 to 8 hours. However, if attempts are made to achieve even lower rates of release with this technique, the release deviates considerably from linearity.

According to B. C. Lippold and H. Förster, Pharm. Ind. 44(7), 735-740 (1982), linear, pH-independent releases of theophylline are obtained by coating theophylline pellets with a lacquer of ethylcellulose and polyethylene glycols. According to statements of the authors, the rate of release from the pellets changes during storage, so that this presentation form also appears to be less than acceptable.

German Offenlegungsschrift No. 2,350,193 proposes pressing a solid porous coating onto tablet cores (containing active compound)by means of a tablet press. A delayed linear release of active compound is said to be achieved by varying the thickness of the coating. This method is unsuitable for a theophylline formulation which is to be administered only once a day, because the tablet, as a result of the amount of auxiliaries required, is too large in size for patient acceptability.

Numerous so-called osmotic release systems are known, for example, from German Patent Specification No. 3,015,870, which release an active compound uniformly and largely independently of external influences. However, formulations designed to release a daily dose of theophylline continuously over a period of up to about 16 hours in the section of the gastrointestinal tract capable of absorption are,in principle, less suitable when they are in the form of a so-called "single unit" dose form. In particular, because of the enormous intra- and interindividual variation in the emptying of the stomach, passage of the formulation through the sections of the gastrointestinal tract essential for absorption are largely accidental and cannot be controlled. "Multiple unit" dose forms consisting of sufficiently small sub-units reflect this dependency of the release of active compound on the emptying of the stomach to a significantly lesser degree, because these sub-units can also pass through the pylorus when the sphincter muscle is closed [H. Bedegaard, Acta Pharm. Technol 28(2), 149-157 (1982)].

It is known from Barnes et al., New Engl. J. Med. 303, 263-267 (1980) that, in asthma patients, various pulmonary function parameters, such as the peak expiratory flow, assume the most unfavorable values in the night between 0200 and 0600 hours. It therefore seems desirable to have available a theophylline-formulation form which provides a theophylline blood level adapted to suit the circadian course of the disease symptoms Such a formulation form should thus produce the highest theophylline levels in the late hours of the night. This is made more difficult by the fact that the absorption of theophylline from the gastrointestinal tract is slowed down during the night.

The results of blood level investigations after a single daily dose of a commercially available "long-term theophylline" are reported by D. Nolte and M. Neumann, Therapiewoche 33, 1138-1141 (1983). The authors state that this formulation leads to considerable individual variations in blood-level values. As a result of these variations, there is a danger that a patient can have sub-therapeutic serum theophylline levels over long periods of the day, and during the night can have serum theophylline levels which are regarded as being in the toxic range (more than 20 $\mu$g/ml).

SUMMARY OF THE INVENTION

The object of the present invention is to provide a sustained-release theophylline formulation which produces plasma theophylline levels in the therapeutic range with a single daily intake, as far as possible, independently of passage and absorption conditions in the gastrointestinal tract, which differ greatly inter- and intra-individually.

This object is achieved by a sustained-release theophylline formulation which comprises matrix pellets in which theophylline particles are embedded in a matrix of water-insoluble plastic and which are enclosed by a membrane of water-insoluble plastic with embedded particles of lactose.

DETAILS

The matrix pellets are advantageously prepared by spraying a suspension of finely-divided theOphylline (in a solution of a water-insoluble plastic in a suitable organic solvent)onto customary inert carrier pellets. Sugar beads, for example, of suitable particle size are used as carrier pellets. The particle size of the carrier pellets is from about 0.2 to 0.5, preferably from 0.3 to 0.4, mm. The matrix pellets are built up using a physiologically-acceptable plastic which is water-insoluble but sufficiently soluble in at least one solvent suitable for pharmaceutical purposes. Its other properties are less critical for the purposes of the present invention. Ethylcellulose is a particularly suitable plastic for the matrix pellets.

Other particularly suitable plastics are, for example, other cellulose ethers, cellulose esters, polyvinyl chloride, polyvinyl alcohol and acrylic acid polymers. It is also possible to employ mixtures of plastics. The amount of the plastic or plastics to be employed is about 2 to 20% by weight of the theophylline, a range from 5 to 10% by weight being preferred.

Advantageous organic solvents for the preparation of the matrix pellets are those which are customary in pharmacy and in which theophylline is insoluble. Among others, the lower alcohols customary in pharmacy, such as ethanol and isopropanol, are suitable. Mixtures of solvents which are miscible with one another, such as a mixture of ethanol and isopropanol, are optionally used. The plastic or the mixture of plastics is dissolved in the chosen solvent or in the solvent mixture. Fine-particled theophylline is then suspended in the resulting solution. It is advantageous to use theophylline with a particle size of less than 50 μm.

The resulting suspension is applied to carrier pellets which are known per se, in particular sugar pellets. The application is carried out, for example, by the immersion tube method familiar to the expert.

Matrix pellets which release theophylline as completely as possible in an aqueous medium within one hour without the matrix structure being destroyed are particularly suitable for the purposes of the present invention. The pellets which remain should appear almost unchanged externally and, when viewed under the microscope in sections, should have a fine-mesh, net-like structure. It is easily possible for the expert to prepare matrix pellets with these properties by simple experiment, by varying the starting substances used and their amounts as well as the preparation parameters.

The membrane is applied to the matrix pellets by spraying thereon a solution of a plastic in a non-aqueous solvent in which lactose is suspended.

Suitable plastics for building up the membrane are those which are water-insoluble, have no or only little swelling capacity in water, are physiologically tolerated and are sufficiently soluble in solvents which are customary in pharmacy. For the purposes of the present invention, plastics with little swelling capacity in water are understood to be those which absorb no more than 5% by weight of water in an aqueous medium. Cellulose ethers and cellulose esters are regarded as particularly suitable plastics for the membrane. In addition, oolymers, such as polyvinyl chloride, are also suitable plastics.

The lactose is preferably employed in micronized form. The particle size is advantageously less than 20 μm, preferably less than 10 μm.

The ratio of plastic to lactose can be varied within wide limits. A weight ratio of plastic to lactose of about 2:1 to 1:3 is preferred. A weight ratio of 4:3 to 4:5 is preferred.

The rate of release of the theophylline can be controlled within a wide range by varying the composition of the membrane and/or by varying the coating thickness of the membrane. Thus, the rate of release is increased by reducing the coating thickness of the membrane, by increasing the content of lactose or by using the lactose in a courser particular form.

The membrane is applied to the matrix pellets in a manner which is known per se, in particular by various spraying techniques. For this, a solution of the plastic or plastic mixture envisaged for the membrane in a solvent or in a solvent mixture is prepared, and the micronized lactose is suspended in this solution, before the spraying operation. If necessary, the suspension is stirred during spraying in order to prevent settling of the suspended lactose.

The membrane optionally contains customary auxiliaries, such as plasticizers, wetting agents and pigments. Pharmacologically-tolerated plasticizers, for example, from the series of phthalic acid, phosphoric acid and citric acid esters and glycerol esters, are suitable Diethyl phthalate is preferably used. Wetting agents are required when the coating is colored with coloring lacquers. Illustrative wetting agens are, for example, sorbitan fatty acid esters or salts of dioctylsulfosuccinic acid.

The new matrix pellets provided with a membrane can in fact also be taken directly, for example, by the spoonful, but a dose form is generally preferred.

The matrix pellets enclosed by a membrane are advantageously contained in capsules, preferably hard gelatin capsules. For dosing, the matrix pellets are either weighed out or divided with dispensing shears or filling devices and introduced into the capsules with capsule-filling apparatus. However, the enclosed matrix pellets are alternatively mixed with suitable auxiliaries and pressed into tablets. Because of the high mechanical stability of the matrix pellets, they are not damaged by a pressing operation. By choosing suitable auxiliaries, such a tablet disintegrates within a few minutes after being taken and releases the matrix pellets in the same way as a capsule.

The object on which the invention is based is achieved in a particularly advantageous manner by mixing matrix pellets according to the invention with different release characteristics.

As described above, the rate of release of the theophllline is controlled within a wide range by varying the composition and coating thickness of the membrane. For example, preparing a 6-hour form (rapid form) and a 12-hour form (slow form) is easily accomplished.

A 6- or 12-hour form is understood here as meaning enclosed matrix pellets which release the active compound continuously over a period of 6 or, respectively, 12 hours in the USP paddle model (pH 7.4, sodium phosphate buffer).

A formulation in which from 30 to 70%, advantageously from 40 to 60% and preferably 50%, by weight of the theophylline daily dose is in the form of enclosed-matrix pellets of the rapid form (for example 6- hour form) and the remainder of the theophylline is in the slow form (for example 12-hour form) gives, when administered, a serum level profile which is adjusted in an optimum manner to suit the circadian course of the asthmatic syndrome. The result thus achieved is that, for example, when a daily dose is taken at about 1900 hours, under steady-state conditions, the serum theophylline level reaches a plateau in the period from about 0200 to about 0700 hours in the morning without entering a toxic range, and, in the subsequent course of the day, remains largely in the therapeutic range until the next base unit is taken. It has also been found that, surprisingly, by using a mixture, the inter- and intraindividual serum level fluctuations, which are already low per se, are reduced even further after a repeated dose. The invention thus particularly preferably relates to theophylline sustainedrelease formulations which consist of a mixture of enclosed matrix pellets with various release characteristics.

If desired, the plateau phase of the serum theophylline level during the night can be increased by increasing the content of enclosed matrix pellets of the slow form.

The expert is thus capable, by combining a "rapid form" with a "slow form", of providing a theophylline sustained release formulation which is to be taken only once daily and which, under steady-state conditions, produces serum-level values adjusted to suit the circadian course of bronchoconstrictory syndromes.

The invention particularly preferably relates to such "mixed" theophylline sustained-release formulations.

Preferred embodiments of such "mixed" theophylline formulations contain enclosed-matrix theophylline pellets of a "slow form" having theophylline release properties, determined in the paddle model according to USP XX at 100 revolutions per minute at a pH of 7.4 (buffer), approximating the cumulative ranges in the following table:

| Hour    | 1st  | 3rd   | 6th   | 9th  |
|---------|------|-------|-------|------|
| Percent | 8–16 | 30–50 | 65–85 | >85, | wherein approximate percent values of 12, 38, 73 and >90, respectively, are preferred and enclosed-matrix theophylline pellets of a "rapid form" having theophylline release properties, determined as before, approximating the cumulative ranges in the following table:

| Hour    | 1st   | 3rd   | 6th  |
|---------|-------|-------|------|
| Percent | 28–40 | 72–92 | >95, | wherein approximate percent values of 34, 82 and 100, respectively, are preferred.

The theophylline matrix pellets, according to the invention, enclosed by a membrane exhibit a largely linear release of theophylline which takes place independently of mechanical stress, pH and surface tension of the test medium. For production on an industrial scale, it is of particular importance that the matrix pellets according to the invention have a surprisingly high batch reproducibility and show no significant change in release properties even after a prolonged storage time under stress conditions.

In pharmacokinetic investigations on volunteers, it is found that, by administering the theophylline sustained-release formulation according to the invention, serum levels which show only a very slight interindividual scatter, which was not hitherto achieved with prior-art formulations, are achieved. In addition, there is an extremely small peak/trough variation, which was not hitherto achieved according to the prior art. In the case of repeated dosing in 24-hour intervals, the so-called swing, as a measure of the variation, is only 50% of that hitherto achieved according to the prior art. With the new sustained-release theophylline formulation, it has become possible, by a single daily dosage under steady-state conditions, to achieve serum theophylline levels which, in comparison with prior art, double the time in the therapeutically-optimum range of from 8 to 15 mg/1.

The invention also relates to embodiments characterized in the patent claims and to processes for preparing sustained-release theophylline formulations according to the invention. The process steps in the preparation processes according to the invention are known per se to the expert.

PREPARATION EXAMPLES

1. Matrix pellets 40 kg of ethylcellulose and 40 kg of polyvinylpyrrolidone are dissolved in a mixture of 800 l of denatured alcohol and 1,200 l of isopropanol. 800 kg of theophylline (particle size <50 μm) are suspended in this solution. This suspension is sprayed onto 89 kg of sugar pellets of particle size 0.3–0.4 mm. 969 kg of theophylline pellets of particle size 0.9–1.1 mm and a theophylline content of 82.5% are obtained. These matrix pellets release theophylline to the extent of 100% in an aqueous medium within 1 hour. The pellet which remains and is almost unchanged externally consists of a finemesh network of ethylcellulose comparable to a Welsbach incandescent mantle.

Instead of ethylcellulose, other water-insoluble physiologically-inert polymers are optionally used. The amount of polymer is varied between 2 and 20% of the theophylline employed. The preferred range is between 5 and 10%. Particularly suitable polymers are: cellulose ethers, cellulose esters, polyvinyl chloride, polyvinyl alcohol and acrylic acid polymers.

2. Enclosing of the matrix pellets

2.1. Starting substances for a batch of 1.5 kg

| (a) | Theophylline matrix pellets | 1,417.50 g |
|-----|------------------------------|------------|
| (b) | Cellulose acetobutyrate (Eastman Kodak, viscosity of a 1% solution in acetone: 0.012 Pa.s) | 37.50 g |
| (c) | Micronized lactose | 41.25 g |
| (d) | Diethyl phthalate | 3.75 g |
| (e) | Acetone | 350 ml |
| (f) | Isopropanol | 350 ml |

2.2 Procedure (b) is dissolved in (e). (c) is suspended in (f) in the course of about 3 minutes with a whirling stirrer (ULTRA-TURRAX® type T45). The solution of (b) in (e) and the suspension of (c) in (f) are combined, with stirring. (d) is then added.

The suspension is sprayed onto the theophylline matrix pellets in a fluidized bed granulator (Aeromatic STREA 1). The suspension is stirred during the spraying process in order to prevent settling of the lactose. After application of the suspension, the matrix pellets are dried for about 30 minutes at an air intake temperature of about 60° C.

2.3. Release properties of the enclosed matrix pellets

The release properties of three different batches A, B and C are determined in the paddle model according to USP XX at 100 revolutions per minute at a pH of 7.4 (buffer):

|           | Approx. Range | Batch A | Batch B | Batch C |
|-----------|---------------|---------|---------|---------|
| 1st hour  | 7–9%          | 7.3%    | 8.2%    | 7.6%    |
| 2nd hour  | 8–9%          | 15.3%   | 16.1%   | 16.4%   |
| 3rd hour  | 8–10%         | 23.8%   | 24.4%   | 25.5%   |
| 4th hour  | 7–9%          | 31.4%   | 32.6%   | 34.4%   |
| 5th hour  | 7–9%          | 39.0%   | 40.5%   | 43.0%   |
| 6th hour  | 7–9%          | 46.2%   | 48.3%   | 51.3%   |
| 7th hour  | 7–8%          | 53.6%   | 55.8%   | 58.8%   |
| 8th hour  | 6–8%          | 60.7%   | 63.1%   | 65.7%   |
| 9th hour  | 6–7%          | 67.2%   | 69.8%   | 71.9%   |
| 10th hour | 5–7%          | 73.6%   | 76.0%   | 77.2%   |
| 11th hour | 4–7%          | 79.9%   | 81.4%   | 81.6%   |
| 12th hour | 3–5%          | 84.4%   | 86.1%   | 85.5%   |

From the release values found it can be seen that a linear release (averaging from 6.5 to 7.5 percent per hour) of active compound over a long period of time together with a very high batch reproducibility can be achieved with the sustained release formulations according to the invention.

3. Control of the release properties of the enclosed micropellets

3.1. Ration of lactose/plastic of 0.5:1

6 g of polyvinyl alcohol and 24 g of ethylcellulose are dissolved in a mixture of 200 g of acetone and 200 g of isopropanol. 15 g of micronized lactose of average particle size 5 μm are suspended in this solution. This suspension is sprayed onto 955 g of theophylline matrix pellets in a fluidized bed spraying apparatus.

A sample is taken, in each case after ⅓, ⅔ and 3/3 of the solution has been sprayed on, to determine the theophylline release. The following results are obtained:

| Hours | Release in % after the coating amount applied is | | |
|---|---|---|---|
|  | ⅓ | ⅔ | 3/3 |
| 1 | 23.4 | 3.3 | 1.0 |
| 2 | 43.4 | 7.5 | 2.4 |
| 3 | 60.8 | 12.0 | 4.2 |
| 4 | 75.4 | 16.3 | 5.6 |
| 5 | 86.3 | 20.8 | 7.4 |
| 6 | 93.6 | 25.2 | 9.2 |
| 7 | 97.0 | 28.8 | 10.6 |

3.2. Ratio of lactose/plastic of 1:1

30 g of ethylcellulose and 4.5 g of triacetin are dissolved in 400 g of ethyl alcohol. 30 g of micronized lactose are suspended in this solution and the suspension is sprayed onto 935.5 g of theophylline matrix pellets in a fluidized bed spraying apparatus. A sample is taken, after 3/6, 4/6, 5/6 and 6/6 of this suspension has been sprayed on, to determine the theophylline release. The following release properties are obtained:

| Hours | Release in % after the coating amount applied is | | | |
|---|---|---|---|---|
|  | 3/6 | 4/6 | 5/6 | 6/6 |
| 1 | 37.5 | 22.8 | 12.5 | 11.4 |
| 2 | 68.1 | 45.6 | 27.0 | 25.0 |
| 3 | 87.8 | 65.7 | 41.8 | 39.0 |
| 4 | 96.6 | 81.6 | 56.4 | 51.9 |
| 5 |  | 90.9 | 68.8 | 64.6 |
| 6 |  |  | 79.2 | 74.1 |
| 7 |  |  | 87.1 | 82.6 |
| 8 |  |  | 92.7 | 88.8 |

3.3 Ratio of lactose/plastic of 3:1

50 g of polyvinyl chloride are suspended in 200 g of acetone, and 200 g of tetrahydrofuran are added. A clear solution is obtained. 150 g of micronized lactose of average particle size 5 μm are suspended in 400 g of acetone. The polymer solution and lactose suspension are combined and sprayed onto 800 g of theophylline matrix pellets in a fluidized bed spraying apparatus. A sample is taken after 10, 6/10, 7/10, 9/10 and 10/10 of this suspension has been sprayed on, to determine the theophylline release. The following release properties are obtained:

| Hours | Release in % after the coating amount applied is | | | | | |
|---|---|---|---|---|---|---|
|  | 4/10 | 6/10 | 7/10 | 8/10 | 9/10 | 10/10 |
| 1 | 66.2 | 54.0 | 47.8 | 42.2 | 32.3 | 30.0 |
| 2 | 98.7 | 85.2 | 77.7 | 69.7 | 60.6 | 57.7 |
| 3 | 109.0 | 102.0 | 96.7 | 89.6 | 84.4 | 79.5 |
| 4 |  | 109.0 | 105.2 | 101.4 | 99.1 | 96.2 |
| 5 |  |  |  | 104.7 | 104.2 | 102.1 |

As the preparation examples given under 3.1. to 3.3. show, the range of the desired theophylline release is very largely controlled by varying the coating thickness of the enclosing membrane and/or by changing the ratio of lactose to plastic in the enclosing membrane.

4. Release properties as a function of the test medium

The following experiments were carried out with a sustained-release theophylline formulation according to the invention and consisting of matrix pellets, such as those described under 1., coated with 3.3% by weight of a membrane consisting of polyvinyl alcohol, ethylcellulose and lactose in a weight ratio of 1:4:5.

4.1. Release properties as a function of the pH

The following table shows the release of theophylline in % by weight in a Eurand-Diffutesterat pH values of 1.2, 6.5 and 7.4. The mean values of n=6 experiments with the standard deviation are given.

| Time | n = 6 pH 1.2 | n = 6 pH 6.5 | n = 6 pH 7.4 |
|---|---|---|---|
| 1st hour | 9.5 ± 0.3 | 9.2 ± 0.4 | 9.7 ± 0.5 |
| 2nd hour | 19.6 ± 0.6 | 17.8 ± 0.6 | 24.3 ± 1.0 |
| 3rd hour | 30.3 ± 0.6 | 27.5 ± 0.8 | 34.0 ± 1.2 |
| 4th hour | 41.4 ± 0.9 | 36.3 ± 0.8 | 43.6 ± 1.5 |
| 5th hour | 51.3 ± 0.8 | 44.9 ± 1.0 | 54.4 ± 1.6 |
| 6th hour | 61.0 ± 1.0 | 53.3 ± 1.3 | 63.2 ± 1.4 |
| 7th hour | 69.7 ± 1.0 | 61.0 ± 1.7 | 71.4 ± 1.7 |
| 8th hour | 77.7 ± 1.1 | 67.8 ± 2.0 | 79.2 ± 1.5 |

4.2 Release properties as a function of the buffer concentration

The following table shows the release of theophylline in % by weight in the USP XX paddle apparatus at 100 revolutions per minute in 0.2, 0.1 and 0.05 molar phosphate buffer (pH 7.4) and in distilled water. The mean values of n=6 experiments with the standard deviation are given.

| Time | Phosphate buffer pH 7.4 0.2 molar | Phosphate buffer pH 7.4 0.1 molar | Phosphate buffer pH 7.4 0.05 molar | Distilled water |
|---|---|---|---|---|
| 1st hour | 8.6 ± 0.3 | 9.8 ± 0.2 | 10.9 ± 0.3 | 9.9 ± 0.3 |
| 2nd hour | 15.8 ± 0.4 | 19.4 ± 0.6 | 20.9 ± 0.8 | 20.1 ± 0.4 |
| 3rd hour | 28.1 ± 0.4 | 28.8 ± 0.8 | 31.2 ± 0.6 | 30.1 ± 1.0 |
| 4th hour | 37.9 ± 0.6 | 39.1 ± 1.0 | 38.1 ± 1.0 | 40.4 ± 0.4 |
| 5th hour | 47.1 ± 0.7 | 48.9 ± 1.3 | 47.6 ± 1.0 | 49.7 ± 0.9 |
| 6th hour | 55.7 ± 0.8 | 58.5 ± 1.7 | 55.4 ± 1.2 | 59.5 ± 1.4 |
| 7th hour | 64.8 ± 0.9 | 68.3 ± 2.0 | 66.1 ± 1.1 | 68.5 ± 1.7 |
| 8th hour | 72.7 ± 0.8 | 76.6 ± 1.8 | 72.5 ± 0.6 | 76.6 ± 1.2 |

4.3. Release properties as a function of surface tension

The following table shows the release of the theophylline in % by weight in a USP XX paddle apparatus at 100 revolutions per minute in 0.1 molar phosphate buffer (pH 7.4) and in the same medium with the addition of 0.1% or 1% of Tween 80.

The mean values from n=6 experiments with the standard deviation are given.

| Time | Phosphate buffer pH 7.4 0.1 molar | Phosphate buffer pH 7.4 0.1 molar +0.1% of Tween 80 | Phosphate buffer pH 7.4 0.1 molar +1% of Tween 80 |
| --- | --- | --- | --- |
| 1st hour | 9.8 ± 0.2 | 9.8 ± 0.3 | 11.5 ± 0.8 |
| 2nd hour | 19.4 ± 0.6 | 19.0 ± 0.5 | 20.8 ± 1.0 |
| 3rd hour | 28.8 ± 0.8 | 29.0 ± 0.7 | 29.2 ± 0.9 |
| 4th hour | 39.1 ± 1.0 | 39.5 ± 1.0 | 38.4 ± 1.1 |
| 5th hour | 48.9 ± 1.3 | 48.0 ± 1.2 | 48.2 ± 1.4 |
| 6th hour | 58.5 ± 1.7 | 56.4 ± 1.3 | 56.4 ± 1.5 |
| 7th hour | 68.3 ± 2.0 | 65.4 ± 1.3 | 65.8 ± 1.8 |
| 8th hour | 76.6 ± 1.8 | 73.4 ± 1.2 | 73.2 ± 1.6 |

The experimental results according to 4.1. to 4.3. show that the enclosed theophylline matrix pellets according to the invention have release properties which are influenced surprisingly little by the pH, the buffer concentration and the surface tension of the test medium.

5. Sustained-release theophylline formulation with release properties adjusted to suit the circadian course of the asthmatic synbdrome 5.1. Slow form Matrix pellets according to Example 1 are coated with a membrane by the process described in Example 2.2, the following amounts of starting substances being used for batch of 4.1 kg:

| | | |
| --- | --- | --- |
| (a) | Theophylline matrix pellets | 3,908.0 g |
| (b) | Cellulose acetobutyrate (Bayer AG, viscosity of a 1% solution in acetone: 0.012 Pa.s) | 92.0 g |
| (c) | Micronized lactose | 92.0 g |
| (d) | Triethyl acetylcitrate | 9.2 g |
| (e) | Acetone | 920.0 ml |
| (f) | Isopropanol | 920.0 ml |

The enclosed matrix pellets continuously release the active compound over a period of 12 hours (12-hour form) in the paddle model according to USP XX at 100 revolutions per minute at a pH of 7.4 (phosphate buffer).

5.2. Rapid form

Matrix pellets according to Example 1 are coated with a membrane by the process described in Example 2.2., the following amounts of starting substances being used for a batch of 4.0 kg:

| | | |
| --- | --- | --- |
| (a) | Theophylline matrix pellets | 3,882.4 g |
| (b) | Cellulose acetobutyrate (Bayer AG, viscosity of a 1% solution in acetone: 0.012 Pa.s) | 56.0 g |
| (c) | Micronized lactose | 56.0 g |
| (d) | Triethyl acetylcitrate | 5.6 g |
| (e) | Acetone | 560.0 ml |
| (f) | Isopropanol | 560.0 ml |

The enclosed matrix pellets continuously release the active compound over a period of 6 hours (6-hour form) in the paddle model according to USP XX at 100 revolutions per minute at a pH of 7.4 (phosphate buffer).

5.3. Study of the serum theophylline level

A theophylline formulation containing, per dosage unit, 400 mg of anhydrous theophylline, 50% of which is in the 12-hour form according to 5.1. and the remainder of which is in the 6-hour form (rapid form according to 5.2.), is prepared. The matrix pellets are introduced into a capsule in a dosage unit.

A study was carried out to determine the steadystate serum theophylline levels which can be achieved with this formulation in comparison with the only theophylline product to be dosed once daily and which is currently commercially available in Germany. The comparison was designed as a randomized multiple-dose cross-over study on healthy male volunteers (nonsmokers, 23 to 33 years old, weighing 69–80 kg). There were two treatment periods, each lasting seven days, with an intermediate wash-out phase likewise of seven days. During the treatment periods, the daily dose of 800 mg of theophylline was, in each case, administered in the evenings at 1900 hours in two capsules of the formulation according to the invention or in two tablets of the comparison product under standardized conditions 36 blood samples were taken from each of the volunteers during each treatment phase. The theophylline content in the samples was determined by means of HPLC (duplicate determination).

Evaluation of the comparison experiment showed that the following surprising advantages are achieved with the formulation according to the invention (called A below) in comparison with the comparison product (called B below), which is recognized as good:

(a) The serum levels under steady-state conditions vary far less significantly with A than with B. In comparison with B, A leads to a swing in the steady-state which is reduced by 51%, swing being understood as the difference between the maximum and minimum serum concentrations in relation to the minimum serum concentration. (Median percentage swing with A 167%, with B 337%; maximum concentration±standard deviation with A 13.4±2.8 mg/1, with B 17.8±4.3 mg/1.)

(b) In comparison with B, A leads to a doubling of the plateau time in the steady-state, that is to say the time within which the theophylline concentration is not more than 1 mg/l below the maximum theophylline concentration. (Average plateau time ± standard deviation with A 5.5±2.1 hours, with B 2.7±1.2 hours).

(c) The period during which the serum theophylline concentration under steady-state conditions is within the range of 8 to 15 mg/l which is desirable as the therapeutic range, above all for the late hours of the night, is 50% longer when A is administered than when B is administered. (A: 14.2±3.3 hours; B 9.6±2.4 hours.)

(d) A causes considerably fewer side effects on the volunteers. This was ascertained by recording the side effects reported by the volunteers. The typical side effects for theophylline of trouble in falling asleep, sleep disturbances, headache, palpitations, increased diuresis, changes in consistency of the stool, tremor and nausea were recorded.

The sums of the products of the frequency of the individual side effects and the severity (scale from 0.5 to 3) on administration of A and B were determined for each volunteer and totaled for all the volunteers to give numerical measures of the individual side effects.

The numerical measures for trouble in falling asleep and sleep disturbances in the case of A reached only 65 and, respectively, 66% of the values of B. Headaches were reduced to 74% on administration of A, palpitations to 43% and increased diuresis to 50%. The side effect of a change in the stool increased to 138%, while tremor and nausea were reduced to 33% and, respectively, 19%.

The invention and its advantages are readily understood from the preceding description. It is apparent that various changes can be made in the products, the method of preparing the products, the actual dosage forms and the method of use without departing from the spirit and scope of the invention or sacrificing its material advantages. The described processes, products and method of use are merely illustrative of preferred embodiments of the invention.

What is claimed is:

1. A pharmacologically-acceptable sustained-release theophylline formulation, which comprises matrix pellets in which theophylline particles are embedded in a matrix of water-insoluble plastic and which are enclosed by a membrane of water-insoluble plastic containing embedded particles of lactose.

2. A sustained-release theophylline formulation as claimed in claim 1, wherein the matrix pellets are built up from inert carrier pellets onto which the matrix containing the theophylline is applied.

3. A sustained-release theophylline formulation as claimed in claim 2, wherein the inert carrier pellets are sugar beads.

4. A sustained-release theophylline formulation as claimed in claim 1, wherein the theophylline particles have a particle size of less than 50 μm.

5. A sustained-release theophylline formulation as claimed in claim 1, wherein the water-insoluble plastic which forms the membrane is not swellable in water.

6. A sustained-release theophylline formulation as claimed in claim 5, wherein the water-insoluble plastic is a cellulose ether or a cellulose ester.

7. A sustained-release theophylline formulation as claimed in claim 1, wherein the particles of lactose embedded in the membrane have a particle size of less than 20 μm.

8. A sustained-release theophylline formulation as claimed in claim 1, which contains half a daily dose of theophylline.

9. A sustained-release theophylline formulation as claimed in claim 1, wherein a plastic in which lactose is insoluble is the p astic which forms the membrane.

10. A sustained-release theophylline formulation as claimed in claim 1, wherein some of the matrix pellets are in a slow form and some of the matrix pellets are in a rapid form.

11. A theophylline formulation as claimed in claim 10, wherein the matrix pellets of the slow form release more than 90%, of the theophylline present in the course of from 10 to 14 hours, preferably 11 to 13 hours in a USP paddle apparatus at pH 7.4, and the matrix pellets of the rapid form release more than 90%, of the theophylline present in the course of 4 to 8, hours in a USP paddle apparatus at pH 7.4.

12. A theophylline formulation as claimed in either claim 10 or claim 11, wherein 30 to 70 % of the theophylline is in the form of matrix pellets of the slow form.

13. A theophylline formulation as claimed in claim 11, which contains 50% of the theophylline as matrix pellets which release more than 95% of the theophylline present in the course of 12 hours in a USP paddle apparatus at pH 7.4, and 50% of the theophylline as matrix pellets which release more than 95% of the theophylline present in the course of 6 hours in a USP paddle apparatus at pH 7.4.

14. A process for the preparation of a sustained-release theophylline formulation, which comprises shaping micronized theophylline into matrix pellets together with a water-insoluble plastic and coating the matrix pellets with a membrane of water-insoluble plastic containing embedded particles of lactose.

15. A process as claimed in claim 14, which comprises spraying a suspension of micronized theophylline in a solution of a water-insoluble plastic in an organic solvent onto carrier pellets to prepare the matrix pellets.

16. A process as claimed in claim 14, which comprises spraying the matrix pellets with a suspension of lactose in an organic-solvent solution of a water-insoluble plastic to coat said pellets.

17. A process as claimed in any one of claims 14, 15 and 16 for the preparation of a sustained-release theophylline formulation, wherein the membrane is a dialysis membrane, and which further comprises preparing the formulation in unit-dosage form.

18. A process as claimed in claim 17, which comprises combining matrix pellets which release the theophylline within 10 to 14 hours with matrix pellets which release the theophylline within 4 to 8 hours.

19. Enclosed-matrix theophylline pellets having 12-hour theophylline release properties, determined in the paddle model according to USP XX at 100 revolutions per minute at a pH of 7.4 (buffer), approximating the ranges in the following table:

| Hour | 1st | 2nd | 3rd | 4th | 5th | 6th | 7th | 8th | 9th | 10th | 11th | 12th |
|---|---|---|---|---|---|---|---|---|---|---|---|---|
| Percent | 7-9 | 8-9 | 9-10 | 7-9 | 7-9 | 7-9 | 7-8 | 6-8 | 6-7 | 5-7 | 4-7 | 3-5 | and averaging from about 6.5 to 7.5 percent release per hour over a 12-hour period.

20. Enclosed-matrix theophylline pellets having theophylline release properties, determined in the paddle model according to USP XX at 100 revolutions per minute at a pH of 7.4 (buffer), approximating the cumulative ranges in the following table:

| Hour | 1st | 3rd | 6th | 9th |
|---|---|---|---|---|
| Percent | 8-16 | 30-50 | 65-85 | >85. |

21. Enclosed-matrix theophylline pellets having theophylline release properties, determined in the paddle model according to USP XX at 100 revolutions per minute at a pH of 7.4 (buffer), approximating the cumulative values in the following table:

| Hour | 1st | 3rd | 6th | 9th |
|---|---|---|---|---|
| Percent | 12 | 38 | 73 | >90. |

22. Enclosed-matrix theophylline pellets having theophylline release properties, determined in the paddle model according to USP XX at 100 revolutions per minute at a pH of 7.4 (buffer), approximating the cumulative ranges in the following table:

| Hour | 1st | 3rd | 6th |
|---|---|---|---|
| Percent | 28-40 | 72-92 | >95. |

23. Enclosed-matrix theophylline pellets having theophylline release properties, determined in the paddle model according to USP XX at 100 revolutions per minute at a pH of 7.4 (buffer), approximating the cumulative values in the following table:

| Hour | 1st | 3rd | 6th |
|---|---|---|---|
| Percent | 34 | 82 | 100. |

24. A process for establishing and maintaining plasma theophylline levels in the therapeutic range over an extended period of time by orally administering a sustained-release formulation, as claimed in claim 1, to a patient in need of such therapy.

25. A sustained-release theophylline formulation as claimed in claim 7, wherein the particles of lactose embedded in the membrane have a particle size of less than 10 μm.

26. A theophylline formulation as claimed in claim 10, wherein the matrix pellets of the slow form release more than 95% of the theophylline present in the course of from 11 to 13 hours in a USP paddle apparatus at pH 7.4, and the matrix pellets of the rapid form release more than 95% of the theophylline present in the course of from 5 to 7 hours in a USP paddle apparatus at pH 7.4.

27. A theophylline formulation according to claim 12 wherein from 40 to 60% of the theophylline is in the form of matrix pellets of the slow form.

28. A pharmacologically-acceptable sustained-release theophylline formulation as claimed in claim 1, wherein the membrane comprises as claimed in claim 1, wherein the membrane comprises a weight ratio of plastic to lactose within a range of from about 2:1 to 1:3.

* * * * *